United States Patent [19]
Perron

[11] 4,152,352
[45] May 1, 1979

[54] PROCESS FOR THE CARBONYLATION OF ARALKYLHALIDES

[75] Inventor: Robert Perron, Charly, France

[73] Assignee: Rhone-Poulenc Industries, Paris, France

[21] Appl. No.: 647,809

[22] Filed: Jan. 9, 1976

[30] Foreign Application Priority Data
Jan. 9, 1975 [FR] France ............................. 75 00533
Sep. 19, 1975 [FR] France ............................. 75 29459

[51] Int. Cl.² .......................................... C07C 179/10
[52] U.S. Cl. .................................. 562/406; 260/465 D
[58] Field of Search .......... 260/502 R, 502 A, 540 R, 260/604 HF, 592 R, 329 R, 515 R, 521 R, 520 R, 515 A, 520 D, 465 D

[56] References Cited
U.S. PATENT DOCUMENTS
3,116,306 12/1963 Huk .................................... 260/410.9
3,928,429 12/1975 El-Chahawi et al. ........... 260/521 R FOREIGN PATENT DOCUMENTS
1016356 1/1966 United Kingdom ................ 260/502 R
1410400 10/1975 United Kingdom ..................... 260/329

Primary Examiner—Werren B. Lone
Attorney, Agent, or Firm—Bacon & Thomas

[57] ABSTRACT

A process for the production of arylpyruvic acids which comprises reacting an arylmethylhalide in a liquid solvent medium with carbon monoxide at pressures of 5 to 200 bars in the presence of a catalytic amount of a metal carbonyl compound and an alkaline earth metal inorganic base.

22 Claims, No Drawings

PROCESS FOR THE CARBONYLATION OF ARALKYLHALIDES

The present invention relates to a process for the carbonylation of aralkyl halides to form an arylpyruvic acid as the predominant product. More particularly, the present invention relates to the carbonylation of arylmethyl halides to form phenylpyruvic acid and other arylpyruvic acids containing, in the aromatic part of their molecules, a substituted benzene ring or condensed benzene rings which may or may not be substituted.

The practical value of such α-keto-carboxylic acids is that they can be used to prepare, in a reducing amination reaction or a selective hydrogenation reaction, the corresponding α-amino-acids or α-hydroxy acids which play an important role in biochemistry. For example, phenylpyruvic acid, can be converted to phenylalanine or 2-hyroxy-3-phenyl-propionic acid.

The preparation of arylpyruvic acids, and especially phenylpyruvic acid, has already been the subject of a large number of investigations and the following methods are available:

rearrangement of phenylglycidic acid using concentrated hydrochloric acid;

dehydration of inactive β-phenylglyceric acid using 50% w/v sulphuric acid or concentrated hydrochloric acid;

acid or alkaline hydrolysis of α-acetaminocinnamic or α-benzoylaminocinnamic acid;

hydrolysis of ethyl phenyloxalacetate;

hydrolysis of a phenylcyanopyruvic ester, or of a mononitrile of the ester of oxalacetic acid, obtained by condensation of benzyl cyanide with ethyl oxalate using sodium;

condensation of an N-diethyloxamic ester with benzyl-magnesium bromide;

action of excess pyridine on a dibrominated derivative of methyl cinnamate and acid hydrolysis of the resulting α,β-dipiperidine derivative; and oxidation of an α-hydroxy-N-tertiary butylamide of 3-phenyl-propionic acid prepared from the corresponding cyanhydrin and acid hydrolysis of the resulting α-keto-N-tertiary butylamide.

It can be seen that the various processes proposed hitherto are somewhat laborious and, because of the diverse treatments which they involve, the processes are difficult to operate on an industrial scale.

We have now found, that it is possible to prepare arylpyruvic acids, simply and with good yields, by carbonylation of arylmethyl halides using carbon monoxide in a liquid solvent medium, in the presence of a carbonylation catalyst and a basic agent.

This means of access to arylpyruvic acids is unexpected. Previously, several processes for the carbonylation of arylmethyl halides to form arylacetic acids have been proposed. U.S. Pat. No. 3,116,306 describes the carbonylation of benzyl chloride and benzyl bromide and of 1-chloromethyl-naphthalene using carbon monoxide at atmospheric pressure or superatmospheric pressure in a solvent medium consisting of a compound containing mobile hydrogen e.g. water, alcohol, an amine, phenol or ammonia in the presence of a salt of a metal-hydrocarbonyl, e.g. sodium cobalt-tetracarbonylate or disodium iron-tetracarbonylate and a base such as an alkali metal or alkaline earth metal hydroxide or carbonate, an alkaline earth metal oxide or tertiary nitrogen-containing base. Belgian Patent No. 807,910 describes the preparation of phenylacetic, para-chlorophenylacetic and para-methylphenylacetic acids by carbonylation of benzyl, para-chlorobenzyl and para-methyl-benzyl chlorides in an aqueous-alcoholic medium using carbon monoxide at atmospheric pressure or superatmospheric pressure in the presence of catalytic amounts of a metal-carbonyl e.g. $Co_2(CO)_8$ or $Fe(CO)_5$ and a basic agent e.g. alkali metal hydroxide or carbonate or alkaline earth metal oxide, hydroxide or carbonate.

Although it is stated in the abovementioned patents that the processes which are described therein lead solely to arylacetic acids (partially in the ester form) and that the results obtained are the same (solely arylacetic acid) no matter what the practical procedures for carrying out the process may be (pressure, nature of the catalyst and nature of the base), it has been found that, by a judicious choice of the CO pressure and of the basic agent employed, it is possible to orientate the carbonylation reaction towards the production of arylpyruvic acids as the major product.

The present invention provides a process for the production of an arylpyruvic acid of the general formula:

$(R)_n$—A—$CH_2$ COCOOH in which:

A represents an aromatic hydrocarbon radical containing 1 or 2 condensed benzene rings, each R, which may be the same or different, represents a linear or branched alkyl radical with up to 4 carbon atoms which is unsubstituted or substituted by a nitro group or by an alkoxy group containing 1 to 4 carbon atoms, or an alkoxy group containing 1 to 4 carbon atoms, or a halogeno, nitrile, nitro or alkylcarbonyloxy group, n is 0 or an integer from 1–3 when A contains one benzene ring, and n is O or an integer from 1–5 when A contains two condensed benzene rings, which comprises carbonylating an arylmethylhalide of the general formula:

$(R)_n$—A—$CH_2$—X       (I)

where R, n and A are as defined above and X represents halogen, by reacting the arylmethyl halide in a liquid solvent medium, with carbon monoxide at a pressure of 5 to 200 bars in the presence of a catalytic amount of a metal carbonyl compound and an alkaline earth metal inorganic base.

R may be, for example, methyl, ethyl, propyl, isopropyl or butyl. Any alkoxy substituents present may be methoxy, ethoxy, propoxy or butoxy.

Preferred arylmethyl halides of the formula (I), which can be used include those in which:

R represents an alkyl radical such as methyl and ethyl, or a fluorine, chlorine, bromine or iodine atom;

n is 0, 1 or 2 when A contains one benzene ring, or is 0, 1, 2 or 3 when A contains 2 condensed benzene rings; and X represents a chlorine or bromine atom.

Specific examples of halides of the formula (I) which can be used in the present invention include: benzyl chloride or bromide, o-, m- or p-methylbenzyl chloride or bromide, 2,3-dimethyl-benzyl chloride or bromide, 2,4-dimethyl-benzyl chloride or bromide, 3,5-dimethyl-benzyl chloride or bromide, o-, m- or p-fluorobenzyl chloride or bromide, o-, m- or p-chlorobenzyl chloride or bromide, and o-, m- or p-bromobenzyl chloride or bromide, 1-chloromethyl-naphthalene, 2-chloromethyl-naphthalene, 1-bromomethyl-naphthalene, 2-bromomethyl-naphthalene, 1-chloromethyl-4-methyl-naphthalene, 1-bromomethyl-5-methyl-naphthalene, 1-chloromethyl-2,3,4-trimethyl-naphthalene, 1-fluoro-2-bromomethyl-naphthalene or 1-methyl-2-bromomethyl-4-fluoro-naphthalene.

The alkaline earth metal inorganic base used in the process may be an alkaline earth metal hydroxide, oxide or carbonate. Suitable basic agents include: $Ca(OH)_2$, $CaO$, $CaCO_3$, $Ba(OH)_2$, $BaCO_3$, $Sr(OH)_2$, $SrO$, $SrCO_3$, $Mg(OH)_2$, $MgO$ and $MgCO_3$. Calcium, barium and strontium hydroxides are particularly suitable.

The amount of basic agent used can vary within wide limits. In general, an amount is used which is at least one mol per mol of arylmethyl halide of the formula (I) employed; the reaction is preferably carried out with an amount larger than this, for example, of the order of 1.1 to 4 mols of base per mol of arylmethyl halide.

It has been found that if, in the process of the invention, the abovementioned alkaline earth metal bases are replaced by alkali metal bases or by tertiary nitrogen-containing bases, and especially NaOH or ethyl diisopropylamine, no formation of arylpyruvic acid then takes place. For CO pressures below 5 bars, for example near atmospheric pressure, the proportion of arylpyruvic acid formed in addition to the arylacetic acid is small, for example of the order of 20% by weight. Only the conjoint use of an alkaline earth metal base and of a CO pressure of between 5 and 200 bars makes it possible to orientate the carbonylation reaction towards the production of arylpyruvic acid as the major product (proportions higher than 50%); within this range, pressures of between 20 and 100 bars are particularly suitable for carrying out the process according to the present invention.

As far as the carbonylation catalyst is concerned, it is possible to use salts of hydrocarbonyls of metals such as iron, cobalt or nickel. It is preferred to use salts of iron-dihydro-tetracarbonyl or salts of cobalt hydro-tetracarbonyl. The radical bonded to the iron-tetracarbonylate or cobalt-tetracarbonylate entities is not critical; for example, they can be metal radicals such as alkali metal (sodium or potassium) or alkaline earth metal (barium) radicals.

Salts which may be used include disodium iron-tetracarbonylate, dipotassium iron-tetracarbonylate, sodium cobalt-tetracarbonylate, potassium cobalt-tetracarbonylate and barium cobalt-tetracarbonylate. Sodium cobalt-tetracarbonylate is generally very suitable for catalysing the reaction.

Salts of metal hydrocarbonyls can be prepared, preferably at the time of their use, by any of the various known processes which have been described in detail. Thus salts of cobalt-hydrotetracarbonyl or salts of iron-dihydro-tetracarbonyl can be prepared by reacting dicobalt-octacarbonyl or iron-pentacarbonyl respectively with a suitable basic agent, and especially an alkali metal or an alkaline earth metal base or a tertiary nitrogen-containing base [compare W. HIEBER and colleagues, Z. Anorg. Allgem. Chem. 232, 17 (1937) and 232, 29 (1937); Ber. 86, 700 (1953); and H. STERNBERG and colleagues, J. Amer. Chem. Soc., 74, 1216 (1952)]. According to the method described in Z. Naturforsch, $13_B$, 192 (1958), it is possible to prepare sodium cobalt-tetracarbonylate or disodium iron-tetracarbonylate by stirring the corresponding metal carbonyl with excess sodium amalgam. The metal hydrocarbonyl salt can be used in the solid state or in the form of its solution in the solvent chosen to carry out the reaction.

Other metal carbonyl derivatives which can be used to carry out the process of the invention, include metal carbonyls such as iron-pentacarbonyl, dicobalt-octacarbonyl and nickel-tetracarbonyl; dicobalt-octacarbonyl is very particularly suitable. These catalysts can be added to the medium in the solid state or also in the form of the solution in the reaction solvent.

The amount of metal-hydrocarbonyl salt or of metal carbonyl used to catalyse the reaction, expressed as the number of gram atoms of metal per mol of arylmethyl halide, can be 0.001 to 1; more precisely, this amount is chosen within the abovementioned range so that it introduces into the reaction medium 0.01 to 0.4 gram atom of metal per mol of arylmethyl halide.

The solvent which can be used in the reaction can be an alcohol, water or alcohol/water mixture.

Examples of alcohols which can be used are saturated, linear or branched, aliphatic monohydroxylic or polyhydroxylic compounds containing 1 to 10 carbon atoms, saturated cycloaliphatic alcohols containing 5 to 12 carbon atoms, and arylaliphatic alcohols. By way of specific examples, the following compounds may be mentioned: methanol, ethanol, propan-1-ol, propan-2-ol, 2-methyl-propan-1-ol, 2-methyl-propan-2-ol, 2,2-dimethyl-propan-1-ol, butan-1-ol, butan-2-ol, 3-methyl-butan-1-ol, 2-methyl-butan-2-ol, 3-methyl-butan-2-ol, pentan-1-ol, pentan-2-ol, pentan-3-ol, ethylene glycol, propane-1,2-diol, butane-1,4-diol, cyclopentanol, cyclohexanol, benzyl alcohol and β-phenylethyl alcohol.

The carbonylation process according to the present invention can be applied particularly well when the reaction is carried out in water/alcohol mixtures. In this preferred group of solvents, mixtures of water with branched aliphatic monohydroxylic compounds corresponding to the criteria listed above are very suitable; examples of such mixtures are: water/propan-2-ol, water/2-methyl-propan-1-ol, water/2-methyl-propan-2-ol, water/2,2-dimethyl-propan-1-ol, water/butan-2-ol, water/3-methyl-butan-1-ol, water/2-methyl-butan-2-ol, water/3-methyl-butan-2-ol, water/pentan-2-ol and water/pentan-3-ol. Water/propan-2-ol mixtures are particularly suitable.

The concentration of the arylmethyl halide of the formula (I) employed in the reaction solvent is not critical and can vary within wide limits; thus it can be between 1 and 40% by weight, but it would be possible to go outside these limits without disadvantage. When the reaction is carried out in water and alcohol, mixtures containing 10 to 60% by weight of water and 90 to 40% by weight of alcohol are generally used.

A practical method of carrying out the process of the invention consists of bringing the mixture, dissolved in the chosen solvent, consisting of the arylmethyl halide, the metal carbonyl catalyst and the alkaline earth metal base, into contact, in a suitable pressure-resistant reactor, with a large excess of carbon monoxide (amount greater than 2 mols of CO per mol of arylmethyl halide) introduced at the desired pressure, in accordance with techniques suitable for bringing about the reaction between a liquid phase and a gas phase.

The carbonylation reaction is carried out at a temperature of 20° C. to 150° C. and preferably 40° C. to 70° C., and is stopped when absorption of CO ceases.

The reaction medium can be treated thereafter in various ways for the purpose of recovering the products resulting from the carbonylation reaction, especially the arylpyruvic acid (main product) and the arylacetic acid (by-product). A preferred treatment consists of filtering an aqueous-alcoholic solution of the crude product resulting from the carbonylation reaction, preferably heated to between 50°–60° C., so as to separate a solid part containing an alkaline earth metal salt of the arylpyruvic acid from an aqueous-alcoholic liquid part containing an alkaline earth metal salt of the arylacetic acid.

The solution containing the crude product resulting from the carbonylation reaction described above can arise directly from the carbonylation of the arylmethyl halide in a water/alcohol medium, and in this particular case it suffices to filter the reaction mixture obtained, at the desired temperature, or it can arise from the addition of water (or alcohol) to the crude product resulting from the carbonylation reaction in an alcoholic (or aqueous) medium.

The solid held back on the filter is then treated with an aqueous solution of an inorganic acid, such as hydrochloric acid, so as to displace the arylpyruvic acid from its alkaline earth metal salt. The solution obtained is extracted with a suitable solvent, for example ether, and the organic extract is then distilled under a pressure which is gradually reduced, without exceeding 40° C. within the mixture. The final residue consists of very pure arylpyruvic acid.

The reaction filtrate can be treated, where appropriate, in order to recover the arylacetic acid which it contains. For example, it is possible to free it from the water and the alcohol and, where appropriate, from the unreacted arylmethyl halide which it contains by distillation at atmospheric pressure. After cooling, the mixture is acidified with an inorganic acid such as HCl and the mixture is then extracted with a suitable solvent, for example ether. The organic extract is then washed with an aqueous alkaline solution and the aqueous wash solution is then acidified and extracted to give, after removing the extraction solvent, a residual mixture containing the arylacetic acid.

The following Examples illustrate the invention.

EXAMPLE 1

200 $cm^3$ of ethyl alcohol, 40 $cm^3$ of water, 31 g (0.418 mol) of calcium hydroxide, 34.1 g (0.270 mol) of benzyl chloride and 1 g (0.0029 mol) of dicobalt-octacarbonyl, corresponding to 0.0058 gram atom of Co, are introduced rapidly into a 0.5 liter stainless steel autoclave equipped with a shaker agitation system.

The reactor is purged 5 times in succession with 20 bars of CO. Agitation is then started up and 50 bars of CO are introduced into the autoclave. The autoclave is heated to a temperature of 60° C. and agitated in this way until absorption of CO ceases. The duration of the reaction is 4 hours and the amount of CO absorbed corresponds to 167% of theory (monocarbonylation).

At the end of this period, the autoclave is degassed and the reaction mixture is then filtered immediately whilst it is still hot. The reactor and the solid on the filter are then washed, one after the other, with 3 times 50 $cm^3$ of water.

(a) Treatment of the solid obtained on the filter

The solid obtained is recovered and introduced into a flask together with 150 $cm^3$ of concentrated hydrochloric acid (density:1.19) and 400 $cm^3$ of water. The mixture is stirred in the presence of 200 $cm^3$ of ether until the solid particles have dissolved completely. The liquid mass is then decanted, and the aqueous phase which is recovered is extracted again twice in succession with 200 $cm^3$ of ether each time. The ether phases are combined and dried over sodium sulphate. After filtration, the solvent is evaporated by heating the solution under a pressure which is gradually reduced, without exceeding 40° C. within the mixture; 32.5 g of a light yellow solid of melting point 171° C. remain.

The results of investigating this product by means of infra-red spectroscopy, nuclear magnetic resonance and mass spectrometry indicate that it is phenylpyruvic acid; the purity of phenylpyruvic acid, measured by acidimetric determination, is 97% by weight.

(b) Treatment of the reaction filtrate

The filtrate is distilled at atmospheric pressure using a 200 mm high column of the VIGREUX type, the temperature of the boiler being 60°–100° C.; the operation is stopped when the temperature at the top of the column reaches 92° C. The reaction mixture is thereafter cooled to a temperature of 25° C., then acidified with 50 $cm^3$ of concentrated hydrochloric acid and extracted three times in succession with 200 $cm^3$ of ether each time. The ether phases are combined and washed with 100 $cm^3$ of a 10% strength by weight aqueous solution of NaOH and then with twice 50 $cm^3$ of water.

The ether phase which has been washed is dried over sodium sulphate; after filtration, the solvent is evaporated by heating the solution under a pressure which is gradually reduced; 0.150 g of an oily liquid remains. The results of investigating this liquid by vapour phase chromatography indicate that it is a mixture of benzyl alcohol (60%) and ethyl phenylacetate (40%).

The alkaline aqueous phase resulting from the washing operation is acidified with 100 $cm^3$ of concentrated hydrochloric acid (density:1.19) and extracted three times in succession with 200 $cm^3$ of ether. The ether phases are combined and dried over sodium sulphate. After filtration, the solvent is removed by heating the solution (temperature below 40° C.) under a pressure which is gradually reduced, and 7.8 g of a white solid are obtained. The results of investigating this solid by vapour phase chromatography (after methylation of an aliquot portion using diazomethane), by acidimetry, and by mass spectrometry, indicate that it is a mixture of phenylacetic acid (86% by weight, corresponding to 6.7 g) and phenylpyruvic acid, α-benzyl-phenylpyruvic acid (or 2-oxo-3-benzyl-3-phenyl-propanoic acid) and α-benzyl-phenylacetic acid (or 2-benzyl-2-phenyl-ethanoic acid).

The final result is as follows: the degree of conversion (DC) of benzyl chloride is quantitative. The yields, expressed relative to the benzyl chloride employed, of phenylpyruvic acid and phenylacetic acid are, respectively, 71.1% and 18.2%.

The ratio of the amounts: phenylpyruvic acid/phenylacetic acid is 3.90.

EXAMPLE 2

The procedure of Example 1 is followed, but sodium cobalt-tetracarbonylate of the formula $NaCo(CO)_4$ is used instead of dicobalt-octacarbonyl.

(a) Preparation of the catalyst 8 g (0.0234 mol) of $Co_2(CO)_8$ and 50 $cm^3$ of ethyldicyclohexylamine are introduced into a 500 $cm^3$ Erlenmeyer flask which is equipped with a stirring system and is placed under nitrogen.

The mixture is stirred for 4 hours at a temperature of about 25° C. 100 cm³ of a N/2 NaOH solution are then added to the mixture which is then stirred for 2 hours, and the reaction mixture is filtered under nitrogen. The filtrate is then decanted and the lower clear colourless aqueous layer, which contains sodium cobalt-tetracarbonylate, is recovered. The volume of the aqueous solution is brought to 200 cm³ exactly.

Determination of the $Co(CO)_4^-$ by means of nickel-o-phenanthroline chloride indicates that the solution contains 0.031 mol of $NaCo(CO)_4$.

(b) Carbonylation reaction 22.6 cm³ (0.0035 mol) of the above aqueous solution of $NaCo(CO)_4$ (0.0035 gram atom of Co) are used and are introduced into the mixture; 17.4 cm³ of water are also added so as to have a total volume of water of 40 cm³.

The balance of the reaction is established as follows:

EXAMPLES 3 TO 5

Investigation of the effect of the pressure.

The carbonylation reaction is carried out as indicated in Example 2, in the presence of sodium cobalt-tetracarbonylate but setting up a CO pressure in the autoclave of 6 bars (Example 3), 20 bars (Example 4) and 100 bars (Example 5).

A comparison experiment involving carbonylation under 1 bar of CO was also carried out (Experiment A).

The results are given in the table below:

| Example/ Experiment | CO pressure bars | Duration hours | Adsorption of CO % of theory (mono-carbonylation) | DC of ⟨O⟩CH₂Cl | Yield based on ⟨O⟩CH₂Cl employed ||  Ratio: I/II |
|---|---|---|---|---|---|---|---|
|  |  |  |  |  | ⟨O⟩CH₂COCOOH (I) | ⟨O⟩CH₂COOH (II) |  |
| 3 | 6 | 5 | 147% | 100% | 45% | 44% | 1.02 |
| 4 | 20 | 5 | 162% | 100% | 57% | 28% | 2.04 |
| 5 | 100 | 4 hrs. 30 mins. | 168% | 100% | 67% | 15% | 4.47 |
| A | 1 | 5 | 78% | 88% | 12% | 51% | 0.23 |

COMPARISON EXPERIMENTS B and C

Investigation of the effect of the nature of the base used.

The carbonylation reaction is carried out:

as indicated in Example 1, in the presence of dicobalt-octacarbonyl, using ethyldiisopropylamine (76 g; 0.590 mol) instead of calcium hydroxide (experiment B), and as indicated in Example 2, in the presence of sodium cobalt-tetracarbonylate, using sodium hydroxide (34 g, 0.850 mol) instead of calcium hydroxide (experiment C).

The working conditions and the results obtained are given in the table below:

| Duration | Adsorption of CO % of theory (monocarbonylation) | DC of ⟨O⟩CH₂Cl | Yield based on ⟨O⟩CH₂Cl employed | | Ratio I/II |
|---|---|---|---|---|---|
|  |  |  | ⟨O⟩CH₂COCOOH (I) | ⟨O⟩CH₂COOH (II) |  |
| 4 hours | 183% | 100% | 72% | 19% | 3.8 |

| EXPERIMENT | B | C |
|---|---|---|
| Catalyst : nature | Co₂(CO)₈ | NaCo(CO)₄ |
| ratio: Co/⟨O⟩CH₂Cl in gram atom/mol | 0.021 | 0.013 |
| Base : nature | C₂H₅N(i-C₃H₇)₂ | NaOH |
| CO pressure in bars | 50 | 50 |
| Temperature | 60° C. | 60° C. |
| Duration in hour | 4 | 3 |
| Absorption of CO : % relative to monocarbonylation | 100% | 100% |
| DC of ⟨O⟩CH₂Cl | 100% | 100% |

Products formed and yields based on

-continued

| EXPERIMENT | B | C |
|---|---|---|
| CH₂Cl employed | | |
| CH₂OH | — | 4% |
| CH₂OC₂H₅ | — | 59% |
| CH₂CO COOH | — | — |
| CH₂COOH | 27% | 36% |
| CH₂COOC₂H₅ | 54% | — |

EXAMPLES 6 TO 12

200 cm³ of propan-2-ol (isopropyl alcohol), 40 cm³ of water, 15.5 g (0.210 mol) of calcium hydroxide, the arylmethyl halide (0.135 mol) used at the rate of:
17.1 g of benzyl chloride (Example 6)
21.7 g of para-chlorobenzyl chloride (Example 7)
19.5 g of ortho-fluorobenzyl chloride (Example 8)
19.5 g of para-fluorobenzyl chloride (Example 9)
19 g of ortho-methylbenzyl chloride (Example 10)
19 g of meta-methylbenzyl chloride (Example 11) and
19 g of para-methylbenzyl chloride (Example 12),
and 0.5 g (0.00145 mol) of dicobalt-octacarbonyl, corresponding to 0.0029 gram atom of Co, are introduced rapidly into a 0.5 liter stainless steel autoclave equipped as in Example 1.

The reactor is purged 5 times in succession with 20 bars of CO. Agitation is then started up and 50 bars of CO are introduced into the autoclave. The autoclave is heated to a temperature of 60° C. and agitated under these conditions until absorption of CO ceases.

Once the carbonylation reaction is complete, the autoclave is degassed and the reaction mixture is then filtered immediately whilst it is still hot. Thereafter the reactor and the solid on the filter are washed, successively, with a mixture of propan-2-ol (200 cm³) and water (40 cm³), this mixture having been heated beforehand to 60° C. The solid on the filter is washed twice more with 30 cm³ of the abovementioned propan-2-ol/water mixture each time.

(a) Treatment of the solid obtained on the filter
The solid obtained is recovered and dried to constant weight at a temperature of about 25° C. under a pressure which is gradually reduced, the final pressure being 0.5 mm of mercury.

The dried solid, weighing 37.9 g (Example 6), 31.8 g (Example 7), 26 g (Example 8), 31 g (Example 9), 37.6 g (Example 10), 30 g (Example 11) and 33.5 g (Example 12), is introduced into a flask together with 100 cm³ of concentrated hydrochloric acid (density:1.19) and 300 cm³ of water. The mixture is stirred in the presence of 200 cm³ of diethyl ether until the solid particles have dissolved completely. The liquid mass is then decanted and the aqueous phase which is recovered is extracted again twice in succession, with 200 cm³ of ether each time. The ether phases are combined and dried over sodium sulphate. After filtration, the solvent is evaporated by heating the solution under a pressure which is gradually reduced, without exceeding 40° C. in the mixture . A white or light yellow crystalline product weighing 18.2 g (Example 6), 19.4 g (Example 7), 18 g (Example 8), 20.6 g (Example 9), 16.4 g (Example 10), 19 g (Example 11) and 20.2 g (Example 12) is thus isolated.

The results of investigating this product by infrared spectroscopy, nuclear magnetic resonance, mass spectrometry and acidimetric determination indicate that it is:

Example 6: phenylpyruvic acid, containing 99% by weight of pure acid,
Example 7: pure (para-chlorophenyl)-pyruvic acid,
Example 8: pure (ortho-fluorophenyl)-pyruvic acid,
Example 9: (para-fluorophenyl)-pyruvic acid, containing 98% by weight of pure acid,
Example 10: (ortho-methylphenyl)-pyruvic acid, containing 97% by weight of pure acid,
Example 11: pure (meta-methylphenyl)-pyruvic acid, and
Example 12: pure (para-methylphenyl)-pyruvic acid.

(b) Treatment of the reaction filtrate
The filtrate obtained at the end of the carbonylation stage is investigated beforehand by vapour phase chromatographic analyses so as to determine the nature and the amount of non-acid compounds which it can contain, namely unreacted arylmethyl chloride starting material, and/or its solvolysis products (such as the corresponding alkylaromatic alcohol and/or isopropyl arylmethyl ether), and/or the isopropyl ester of the arylacetic acid formed.

The following table indicates the nature and the amount of these non-acid compounds for each of the experiments carried out:

| | Unreacted arylmethy chloride | Solvolysis products | Isopropyl ester of the arylacetic acid |
|---|---|---|---|
| Example 6 | ⟨phenyl⟩—CH₂Cl : 0.49 g | — | ⟨phenyl⟩—CH₂COOC₃H₇ : 0.67 g |
| Example 7 | — | — | Cl—⟨phenyl⟩—CH₂COOC₃H₇ : 1.15 g |
| Example 8 | (o-F)⟨phenyl⟩—CH₂Cl : 0.3 g | — | (o-F)⟨phenyl⟩—CH₂COOC₃H₇ : 0.4 g |
| Example 9 | F—⟨phenyl⟩—CH₂Cl : 0.2 g | — | F—⟨phenyl⟩—CH₂COOC₃H₇ : 0.49 g |
| Example 10 | — | — | — |
| Example 11 | (m-CH₃)⟨phenyl⟩—CH₂Cl : 0.28 g | — | (m-CH₃)⟨phenyl⟩—CH₂COOC₃H₇ : 0.9g |
| Example 12 | — | CH₃—⟨phenyl⟩—CH₂OC₃H₇ : 0.33 g | CH₃—⟨phenyl⟩—CH₂COOC₃H₇ : 0.37 g |

Treatment 200 cm³ of water are added to the filtrate and the whole is then distilled at atmospheric pressure using a 200 mm high VIGREUX column, the temperature of the boiler being 60°–110° C.; the operation is stopped when the temperature at the top of the column reaches 95° C.–100° C. The reaction mixture is thereafter cooled to a temperature of 25° C., then acidified with concentrated hydrochloric acid (density:1.19) and extracted three times in succession with 200 cm³ of ether each time. The ether phases are combined and washed with 100 cm³ and then with 50 cm³ of a 10% strength by weight aqueous solution of NaOH and then with twice 50 cm³ of water.

The alkaline aqueous phase resulting from the washing process is acidified with 50 cm³ of concentrated hydrochloric acid (density:1.19) and extracted three times in succession with 200 cm³ of ether. The ether phases are combined and dried over sodium sulphate. After filtration, the solvent is removed by heating the solution under a pressure which is gradually reduced, and 1.2 g of a solid (Example 6), 3.1 g of a paste-like mass (Example 7), 4.4 g of an oily liquid (Example 8), 2.1 g of an oily liquid (Example 9), 5 g of an oily liquid (Example 10), 1.8 g of a paste-like mass (Example 11) and 1.9 g of a crystalline solid (Example 12) are obtained.

The results of investigating these products by vapour phase chromatography (after methylation of an aliquot portion using diazomethane), by acidimetry and by mass spectrometry indicate that what is involved is a mixture of arylacetic acid and acids of the type:

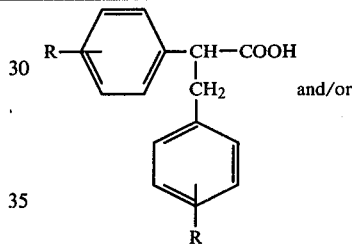

and/or

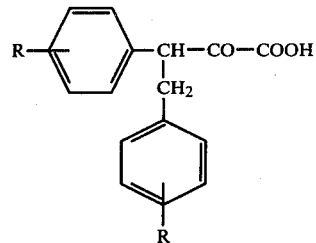

R representing hydrogen or the substituent carried by the benzene ring of the arylmethyl halide starting material.

More particularly, it is found that the mixture obtained contains:

Example 6: 76% by weight (0.91 g) of phenylacetic acid;

Example 7: 85% by weight (2.64 g) of (para-chlorophenyl)-acetic acid;

Example 8: 25% by weight (1.10 g) of (ortho-fluorophenyl)-acetic acid;

Example 9: 47% by weight (0.99 g) of (para-fluorophenyl)-acetic acid;

Example 10: 8% by weight (0.4 g) of (ortho-methylphenyl)-acetic acid;

Example 11: 58% by weight (1 g) of (meta-methylphenyl)-acetic acid; and

Example 12: 23% by weight (0.44 g) of (para-methylphenyl)-acetic acid.

The balance of the reaction is established as follows:

|  | Duration in hours | Absorption of CO % relative to mono-carbonylation | DC of R—⌬—CH₂Cl | Yields based on R—⌬—CH₂Cl employed  R—⌬—CH₂COCOOH (I) | R—⌬—CH₂COOH (II)  | Ratio I/II |
|---|---|---|---|---|---|---|
| Example | | | | | | |
| 6 R=H | 4 | 187% | 97% | 82.2% | 2.5% | 32.8 |
| 7 R=Cl in the para-position | 4 | 200% | 100% | 73% | 12% | 6.1 |
| 8 R=F in the ortho-position | 4 | 193% | 98% | 73% | 5% | 14.6 |
| 9 R=F in the para-position | 4 | 200% | 99% | 81.2% | 5.9% | 13.8 |
| 10 R=CH₃ in the ortho-position | 4 | 200% | 100% | 66% | 2% | 33 |
| 11 R=CH₃ in the meta-position | 4 | 183% | 98.5% | 79% | 5% | 15.8 |
| 12 R=CH₃ in the para-position | 4 | 200% | 100% | 84% | 1.6% | 52.5 |

What we claim is:

1. A process for the production of an arylpyruvic acid of the general formula:

$(R)_n$—A—$CH_2$ COCOOH in which:
A represents an aromatic hydrocarbon radical having 1 benzene ring or 2 condensed benzene rings,
each R, which may be the same or different, represents (i) a linear or branched alkyl radical with up to 4 carbon atoms said alkyl radical being unsubstituted or substituted by a nitro group or by an alkoxy group containing 1 to 4 carbon atoms, (ii) an alkoxy group containing 1 to 4 carbon atoms, (iii) a halogeno, (iv) nitrile or (v) nitro,
n is 0 or an integer from 1–3 when A represents one benzene ring, and n is 0 or an integer from 1–5 when A represents two condensed benzene rings, which comprises carbonylating an arylmethylhalide of the general formula $(R)_n$—A—$CH_2$—X where R, n and A are as defined above and X represents halogen, and producing a major amount of said arylpyruvic acid, by reacting the arylmethyl halide at a temperature of from 50° C. to 150° C., in a liquid solvent medium selected from water, alcohol or water/alcohol mixtures, with carbon monoxide at a pressure of 5 to 200 bars in the presence of a catalytic amount of a cobalt, iron or nickel carbonyl compound and an alkaline earth metal inorganic base wherein said inorganic base is an alkaline earth metal hydroxide, oxide or carbonate.

2. A process according to claim 1, wherein
R represents a methyl or ethyl group, or fluorine, chlorine, bromine or iodine, and
n is 0 or 1 or 2 when A represents one benzene ring, and is 0, 1, 2 or 3 when A represents two condensed benzene rings, and
X represents chlorine or bromine.

3. A process according to claim 2, wherein the arylmethyl halide is benzyl chloride or bromide, o-, m- or p-methylbenzyl chloride or bromide, 2,3-dimethyl-benzylchloride or bromide, 2,4-dimethyl-benzyl chloride or bromide, 3,5-dimethyl-benzyl chloride or bromide, o-, m- or p-fluorobenzyl chloride or bromide, o-, m- or p-chlorobenzyl chloride or bromide, o-, m- or p-bromobenzyl chloride or bromide, 1-chloromethylnaphthalene, 2-chloromethylnaphthalene, 1-bromomethylnaphthalene, 2-bromomethylnaphthalene, 1-chloromethyl-4-methyl-naphthalene, 1-bromomethyl-5-methyl-naphthalene, 1-chloromethyl-2,3,4-trimethyl-naphthalene, 1-fluoro-2-bromo-methyl-naphthalene or 1-methyl-2-bromomethyl-4-fluoro-naphthalene.

4. A process according to claim 1, wherein the carbon monoxide pressure is 20 to 100 bars.

5. A process according to claim 1, wherein the base is $Ca(OH)_2$, CaO, $CaCO_3$, $Ba(OH)_2$, BaO, $BaCO_3$, $Sr(OH)_2$ SrO, $SrCO_3$, $Mg(OH)_2$, MgO or $MgCO_3$.

6. A process according to claim 5, wherein the base is $Ca(OH)_2$, $Ba(OH)_2$ or $Sr(OH)_2$.

7. A process according to claim 1, wherein the amount of inorganic base is 1 to 4 mols per mol of arylmethyl halide.

8. A process according to claim 1, wherein the carbonylation catalyst is a salt of a hydrocarbonyl of iron, cobalt or nickel.

9. A process according to claim 8, wherein the carbonylation catalyst is a salt of cobalt-hydro-tetracarbonyl or a salt of iron-dihydro-tetracarbonyl.

10. A process according to claim 9, wherein the salt used is sodium cobalt-tetracarbonylate.

11. A process according to claim 1, wherein the carbonylation catalyst is $Fe(CO)_5$, $Co_2(CO)_8$ or $Ni(CO)_4$.

12. A process according to claim 11, wherein the metal carbonyl is dicobalt-octacarbonyl.

13. A process according to claim 1, wherein the amount of metal carbonyl catalyst is chosen so that it introduces into the carbonylation medium 0.001 to 1 gram atom of metal per mol of arylmethyl halide.

14. A process according to claim 13, wherein the catalyst introduces 0.01 to 0.4 gram atom of metal per mol of arylmethyl halide.

15. Process according to claim 1, wherein the alcohol is a saturated, linear or branched, aliphatic, monohydroxylic or polyhydroxylic compound containing up to 10 carbon atoms, a saturated cycloaliphatic alcohol containing 5 to 12 carbon atoms or an arylaliphatic alcohol.

16. Process according to claim 1, wherein the reaction is carried out in water/alcohol mixtures.

17. Process according to claim 16, wherein the mixture consists of water and a saturated branched aliphatic monohydroxylic compound.

18. A process according to claim 1, wherein the temperature is 40° C. to 70° C.

19. Process according to claim 1, wherein the arylpyruvic acid is recovered from the crude reaction product by filtering an aqueous-alcoholic solution of the crude product so as to separate a solid part containing an alkaline earth metal salt of the arylpyruvic acid from an aqueous-alcoholic liquid phase containing an alkaline earth metal salt of the arylacetic acid, the arylpyruvic acid being then displaced from its salt by acidification using an aqueous solution of an inorganic acid.

20. A process according to claim 19, wherein the solution of crude reaction product is filtered at 50°-60° C.

21. The process according to claim 1, wherein said liquid solvent medium is alcohol.

22. The process according to claim 1, wherein said arylmethyl halide reactant is benzyl chloride and said arylpyruvic acid product is phenylpyruvic acid.

* * * * *